(12) United States Patent
Fukuda

(10) Patent No.: US 11,488,333 B2
(45) Date of Patent: Nov. 1, 2022

(54) IMAGE PROCESSING SYSTEM, IMAGE PROCESSING METHOD, AND IMAGE PROCESSING PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 19 days.

(21) Appl. No.: 16/899,459

(22) Filed: Jun. 11, 2020

(65) Prior Publication Data

US 2021/0019922 A1 Jan. 21, 2021

(30) Foreign Application Priority Data

Jul. 16, 2019 (JP) .............................. JP2019-131393

(51) Int. Cl.
*G06T 11/00* (2006.01)
*A61B 6/00* (2006.01)
(Continued)

(52) U.S. Cl.
CPC .............. *G06T 11/003* (2013.01); *A61B 6/03* (2013.01); *A61B 6/461* (2013.01); *G06T 7/50* (2017.01); *A61B 6/502* (2013.01)

(58) Field of Classification Search
CPC ... G06T 11/003; G06T 7/50; G06T 2211/436; G06T 11/006; A61B 6/03; A61B 6/461; A61B 6/502; A61B 6/0414; A61B 6/025
See application file for complete search history.

(56) References Cited

U.S. PATENT DOCUMENTS

| | | |
|---|---|---|
| 8,983,156 B2 | 3/2015 | Periaswamy et al. |
| 2009/0123052 A1 | 5/2009 | Ruth et al. |

(Continued)

FOREIGN PATENT DOCUMENTS

| | | |
|---|---|---|
| JP | 2006-296646 A | 11/2006 |
| JP | 2014128716 A | 7/2014 |

(Continued)

OTHER PUBLICATIONS

The extended European search report issued by the European Patent Office dated Dec. 2, 2020, which corresponds to European Patent Application No. 20180918.3-1122 and is related to U.S. Appl. No. 16/899,459.

(Continued)

*Primary Examiner* — Courtney D Thomas
(74) *Attorney, Agent, or Firm* — Studebaker & Brackett PC

(57) ABSTRACT

An image processing system comprising includes: an acquisition unit that acquires a plurality of projection images obtained by tomosynthesis imaging in which radiation is emitted from a radiation source to a breast at different irradiation angles and a projection image is captured at each irradiation angle by a radiation detector; a tomographic image generation unit that generates a plurality of tomographic images in each of a plurality of tomographic planes of the breast, from the plurality of projection images; a composite two-dimensional image generation unit that generates a composite two-dimensional image from a plurality of images selected from among the plurality of projection images and the plurality of tomographic images; an information generation unit that generates correspondence relationship information representing a correspondence relationship between a position in the composite two-dimensional image and a depth of a tomographic plane corresponding to the position; a display controller that performs control of causing a display device to display the composite two-dimensional image; an acceptance unit that accepts region information representing a designated region designated with respect to the composite two-dimensional image displayed on the display device; and a designated tomographic image generation unit that generates, as a designated tomographic image, a tomographic image in a tomographic plane (Continued)

at a depth which corresponds to the designated region in the composite two-dimensional image and is specified on the basis of the correspondence relationship information, in a case where the acceptance unit accepts the region information, wherein in a case where the designated tomographic image is generated, the display controller further performs control of causing the display device to display the generated designated tomographic image.

12 Claims, 13 Drawing Sheets

(51) Int. Cl.
    *G06T 7/50*     (2017.01)
    *A61B 6/03*     (2006.01)

(56) References Cited

U.S. PATENT DOCUMENTS

| | | |
|---|---|---|
| 2015/0052471 A1 | 2/2015 | Chen et al. |
| 2016/0066872 A1* | 3/2016 | Kreeger ............... A61B 6/463 345/419 |
| 2016/0089098 A1 | 3/2016 | Nakayama et al. |
| 2016/0095563 A1 | 4/2016 | Fukuda et al. |
| 2018/0089098 A1 | 3/2018 | Guim Bernat et al. |
| 2018/0256126 A1 | 9/2018 | Fukuyo et al. |

FOREIGN PATENT DOCUMENTS

| | | |
|---|---|---|
| JP | 2016-067414 A | 5/2016 |
| JP | 2016-067695 A | 5/2016 |
| JP | 6208731 B2 | 10/2017 |
| JP | 2018-047256 A | 3/2018 |
| WO | 2014203531 A1 | 12/2014 |

OTHER PUBLICATIONS

An Office Action; "Notice of Reasons for Refusal," mailed by the Japanese Patent Office dated Aug. 2, 2022, which corresponds to Japanese Patent Application No. 2019-131393 and is related to U.S. Appl. No. 16/899,459, with English language translation.

\* cited by examiner

IMAGE PROCESSING SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2019-131393 filed on Jul. 16, 2019. The above application is hereby expressly incorporated by reference, in its entirety, into the present application.

BACKGROUND

1. Technical Field

The present disclosure relates to an image processing system, an image processing method, and an image processing program.

2. Description of the Related Art

In general, a technique in which a doctor interprets a radiographic image captured by a mammography apparatus to perform diagnosis of a lesion or the like of the breast is known. As this type of radiographic images, a plurality of projection images obtained by the so-called tomosynthesis imaging, and a tomographic image generated by performing reconstruction processing on a plurality of projection images are known. As the main radiographic image, a composite two-dimensional image generated from a plurality of images selected from among a plurality of projection images and a plurality of tomographic images is known.

In the image interpretation, diagnosis is performed by mutually referring to a tomographic image and a two-dimensional radiographic image such as a composite two-dimensional image, in some cases. For example, WO2014/203531A discloses a technique of creating a depth map in which each position on a composite two-dimensional image and depth information indicating a position in a depth direction of a tomographic plane corresponding to each position are associated, and extracting and displaying a tomographic image corresponding to the depth of a specific position in a case where the specific position is designated on the composite two-dimensional image.

SUMMARY

In the technique disclosed in WO2014/203531A, in case of image interpretation, a plurality of tomographic images that can be referred to by an interpreter are required. In general, since tomographic images contain a large amount of information in the image and the number of images is relatively large, a large storage capacity is required in order to store a plurality of tomographic images which are prepared to be referable, in some cases. Further, for example, in a case where such a plurality of tomographic images are generated in real time according to the image interpretation of the interpreter, the processing time becomes increased, or a processing load of an image processing apparatus that generates tomographic images becomes increased in some cases.

In this manner, in the technique in the related art, in a case where diagnosis is performed by mutually referring to the composite two-dimensional image and the tomographic image, the load associated with the handling of tomographic images is large in some cases.

The present disclosure is made in view of the above-described circumstances, and an object of the present disclosure is to provide an image processing apparatus, an image processing method, and an image processing program which can reduce a load associated with the handling of tomographic images.

In order to achieve the object, an image processing system according to a first aspect of the present disclosure comprises an acquisition unit that acquires a plurality of projection images obtained by tomosynthesis imaging in which radiation is emitted from a radiation source to a breast at different irradiation angles and a projection image is captured at each irradiation angle by a radiation detector; a tomographic image generation unit that generates a plurality of tomographic images in each of a plurality of tomographic planes of the breast, from the plurality of projection images; a composite two-dimensional image generation unit that generates a composite two-dimensional image from a plurality of images selected from among the plurality of projection images and the plurality of tomographic images; an information generation unit that generates correspondence relationship information representing a correspondence relationship between a position in the composite two-dimensional image and a depth of a tomographic plane corresponding to the position; a display controller that performs control of causing a display device to display the composite two-dimensional image; an acceptance unit that accepts region information representing a designated region designated with respect to the composite two-dimensional image displayed on the display device; and a designated tomographic image generation unit that generates, as a designated tomographic image, a tomographic image in a tomographic plane at a depth which corresponds to the designated region in the composite two-dimensional image and is specified on the basis of the correspondence relationship information, in a case where the acceptance unit accepts the region information, in which in a case where the designated tomographic image is generated, the display controller further performs control of causing the display device to display the generated designated tomographic image.

In an image processing system according to a second aspect of the present disclosure, in the image processing system according to the first aspect, the designated tomographic image is a tomographic image of a portion corresponding to the designated region, in the tomographic plane at the depth specified according to a position of the designated region.

In an image processing system according to a third aspect of the present disclosure, in the image processing system according to the first aspect, the designated tomographic image is a tomographic image including an image of the entire breast, in the tomographic plane at the depth specified according to a position of the designated region.

In an image processing system according to a fourth aspect of the present disclosure, in the image processing system according to the first aspect, the designated tomographic image is a tomographic image of a portion corresponding to a region in a predetermined range including the designated region, in the tomographic plane at the depth specified according to a position of the designated region.

In an image processing system according to a fifth aspect of the present disclosure, in the image processing system according to the first aspect, the designated tomographic image generation unit further generates tomographic images in tomographic planes at predetermined depths before and after the depth of the designated tomographic image, and the display controller further performs control of causing the display device to display the generated tomographic images in the tomographic planes at the depths before and after the depth of the designated tomographic image.

In an image processing system according to a sixth aspect of the present disclosure, in the image processing system according to the first aspect, the display controller performs control of causing the display device to display the composite two-dimensional image and the designated tomographic image side by side.

In an image processing system according to a seventh aspect of the present disclosure, in the image processing system according to the first aspect, the display controller performs control of causing the display device to display the composite two-dimensional image and the designated tomographic image in a state in which the composite two-dimensional image and the designated tomographic image are at least partially superimposed on each other.

An image processing system according to an eighth aspect of the present disclosure, in the image processing system according to the first aspect, further comprises a storage controller that performs control of deleting the plurality of tomographic images from a storage unit, in a case where the plurality of tomographic images are stored in the storage unit after the composite two-dimensional image and the correspondence relationship information are generated.

An image processing system according to a ninth aspect of the present disclosure, in the image processing system according to the first aspect, further comprises an image processing apparatus that includes a transmission unit that transmits the composite two-dimensional image, the correspondence relationship information, and the designated tomographic image to the display device, the acquisition unit, the tomographic image generation unit, the composite two-dimensional image generation unit, the information generation unit, and the designated tomographic image generation unit; and the display device that includes a reception unit that receives the composite two-dimensional image, the correspondence relationship information, and the designated tomographic image from the image processing apparatus, the display controller, and the acceptance unit.

An image processing system according to a tenth aspect of the present disclosure, in the image processing system according to the first aspect, further comprises an image processing apparatus that includes a transmission unit that transmits the plurality of projection images, the composite two-dimensional image, and the correspondence relationship information, to the display device, the acquisition unit, the tomographic image generation unit, the composite two-dimensional image generation unit, and the information generation unit; and the display device that includes a reception unit that receives the plurality of projection images, the composite two-dimensional image, and the correspondence relationship information from the image processing apparatus, the designated tomographic image generation unit, the display controller, and the acceptance unit.

Further, in order to achieve the object, an image processing method according to an eleventh aspect of the present disclosure is a method executed by a computer, and comprises acquiring a plurality of projection images obtained by tomosynthesis imaging in which radiation is emitted from a radiation source to a breast at different irradiation angles and a projection image is captured at each irradiation angle by a radiation detector; generating a plurality of tomographic images in each of a plurality of tomographic planes of the breast, from the plurality of projection images; generating a composite two-dimensional image from a plurality of images selected from among the plurality of projection images and the plurality of tomographic images; generating correspondence relationship information representing a correspondence relationship between a position in the composite two-dimensional image and a depth of a tomographic plane corresponding to the position; performing control of causing a display device to display the composite two-dimensional image; accepting region information representing a designated region designated with respect to the composite two-dimensional image displayed on the display device; generating, as a designated tomographic image, a tomographic image in a tomographic plane at a depth which corresponds to the designated region in the composite two-dimensional image and is specified on the basis of the correspondence relationship information, in a case where the region information is accepted; and further performing control of causing the display device to display the generated designated tomographic image, in a case where the designated tomographic image is generated.

Further, in order to achieve the object, a non-transitory computer-readable storage medium storing an image processing program according to a twelfth aspect of the present disclosure causes a computer to execute a process comprising acquiring a plurality of projection images obtained by tomosynthesis imaging in which radiation is emitted from a radiation source to a breast at different irradiation angles and a projection image is captured at each irradiation angle by a radiation detector; generating a plurality of tomographic images in each of a plurality of tomographic planes of the breast, from the plurality of projection images; generating a composite two-dimensional image from a plurality of images selected from among the plurality of projection images and the plurality of tomographic images; generating correspondence relationship information representing a correspondence relationship between a position in the composite two-dimensional image and a depth of a tomographic plane corresponding to the position; performing control of causing a display device to display the composite two-dimensional image; accepting region information representing a designated region designated with respect to the composite two-dimensional image displayed on the display device; generating, as a designated tomographic image, a tomographic image in a tomographic plane at a depth which corresponds to the designated region in the composite two-dimensional image and is specified on the basis of the correspondence relationship information, in a case where the region information is accepted; and further performing control of causing the display device to display the generated designated tomographic image, in a case where the designated tomographic image is generated.

Further, an image processing system according to an aspect of the present disclosure is an image processing system having a processor, and the processor acquires a plurality of projection images obtained by tomosynthesis imaging in which radiation is emitted from a radiation source to a breast at different irradiation angles and a projection image is captured at each irradiation angle by a radiation detector; generates a plurality of tomographic images in each of a plurality of tomographic planes of the breast, from the plurality of projection images; generates a composite two-dimensional image from a plurality of images selected from among the plurality of projection images and the plurality of tomographic images; generates correspondence relationship information representing a correspondence relationship between a position in the composite two-dimensional image and a depth of a tomographic plane corresponding to the position; performs control of causing a display device to display the composite two-dimensional image; accepts region information representing a designated region designated with respect to the composite two-dimensional image displayed on the display device; generates, as a designated tomographic image, a tomographic image in a tomographic plane at a depth which corresponds to the designated region in the composite two-dimensional image and is specified on the basis of the correspondence relationship information, in a case where the region information is accepted; and further performs control of causing the display device to display the generated designated tomographic image, in a case where the designated tomographic image is generated.

According to the present disclosure, it is possible to reduce a load associated with the handling of tomographic images.

DETAILED DESCRIPTION

Hereinafter, embodiments of the present disclosure will be described in detail with reference to the drawings. The embodiments do not limit the present disclosure.

First Embodiment

Figure 1:
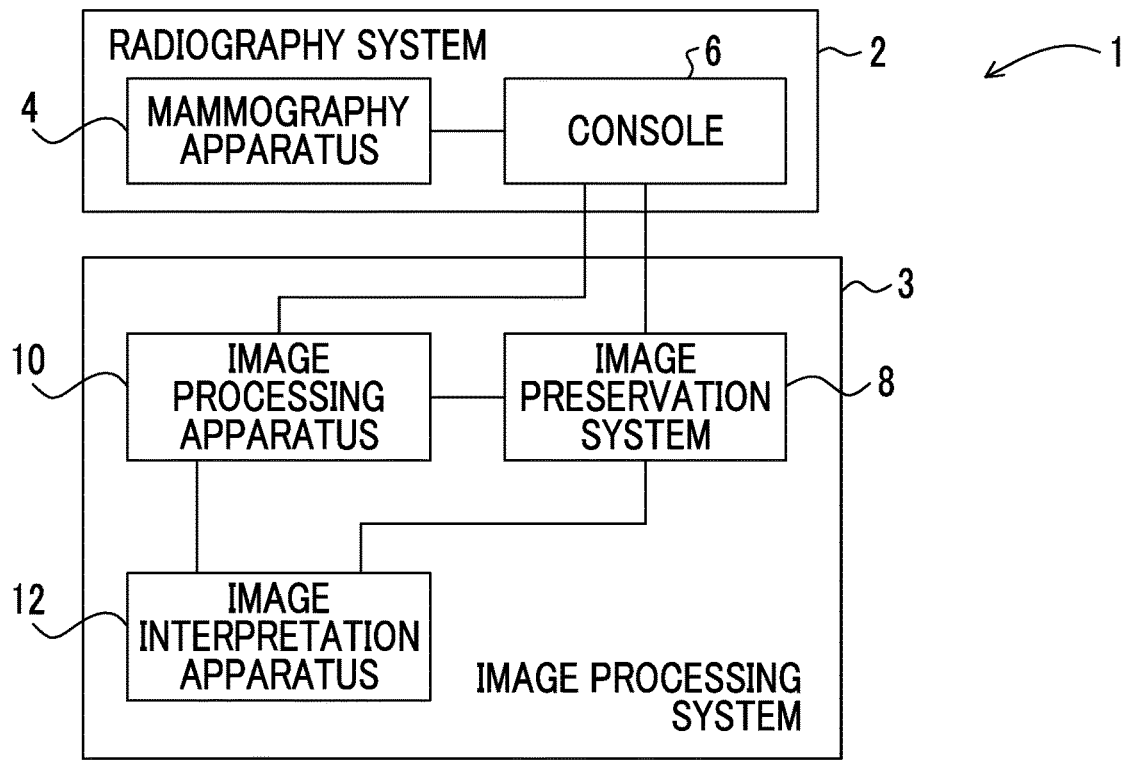
FIG. 1 is a configuration diagram schematically illustrating an example of the overall configuration of a medical system of a first embodiment.

First, an example of the overall configuration of a medical system comprising an image processing system of the embodiment will be described. FIG. 1 is a configuration diagram illustrating an example of the overall configuration of a medical system 1 of the embodiment.

As illustrated in FIG. 1, the medical system 1 of the embodiment comprises a radiography system 2 and an image processing system 3.

The radiography system 2 includes a mammography apparatus 4 and a console 6.

The console 6 of the embodiment has a function of controlling the mammography apparatus 4 using, for example, an imaging order and various kinds of information acquired from a radiology information system (RIS) (not illustrated) through a wireless communication local area network (LAN) and an instruction or the like directly performed by a technician or the like. As an example, in the embodiment, a server computer is used as the console 6.

On the other hand, the mammography apparatus 4 of the embodiment comprises a radiation source and a radiation detector (which are not illustrated). The mammography apparatus 4 irradiates the breast of a subject as an object with radiation (for example, X-rays) using the radiation source to capture a radiographic image of the breast using the radiation detector under the control of the console 6. In addition, the mammography apparatus 4 may be an apparatus that images the breast of the subject not only in a state in which the subject is standing (standing position state) but also in a state in which the subject sits on a chair (including a wheelchair) or the like (sitting position state). In the embodiment, a plurality of types of radiographic images, such as a projection image, a tomographic image, and a composite two-dimensional image will be referred to, but in case of collectively referring to the images without distinguishing the types thereof, the plurality of types of radiographic images are simply referred to as a "radiographic image".

In the mammography apparatus 4 of the embodiment, a plurality of types of imaging can be performed for capturing a radiographic image. Specifically, the mammography apparatus 4 can perform, on the breast, two types of so-called simple imaging of cranio-caudal (CC) imaging where the imaging direction is a craniocaudal direction, and medio-lateral oblique (MLO) imaging where the imaging direction is a mediolateral oblique direction Further, the mammography apparatus 4 of the embodiment can perform tomosynthesis imaging in which radiation is emitted from the radiation source to the breast at different irradiation angles and a projection image is captured at each irradiation angle by the radiation detector.

Meanwhile, the image processing system 3 of the embodiment includes an image preservation system 8, an image processing apparatus 10, and an image interpretation apparatus 12.

First, the configuration of the image preservation system 8 will be described.

The image preservation system 8 of the embodiment is a system that preserves image data of the radiographic image captured by the radiography system 2 and image data of the radiographic image generated by the image processing apparatus 10. The image preservation system 8 extracts an image corresponding to a request from, for example, the console 6, the image processing apparatus 10, and the image interpretation apparatus 12 from the preserved radiographic images, and transmits the extracted image to the apparatus which is a request source. A specific example of the image preservation system 8 is picture archiving and communication systems (PACS).

Figure 2:
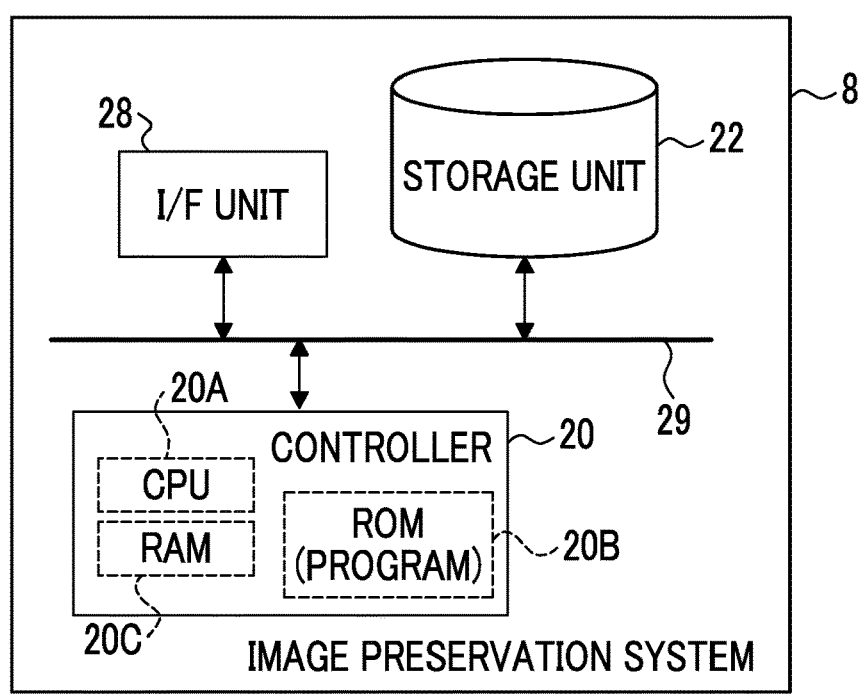
FIG. 2 is a block diagram illustrating an example of the configuration of an image preservation system of the first embodiment.

FIG. 2 is a block diagram illustrating an example of the image preservation system 8 of the embodiment. As illustrated in FIG. 2, the image preservation system 8 of the embodiment comprises a controller 20, a storage unit 22, and an interface (I/F) unit 28. The controller 20, the storage unit 22, and the I/F unit 28 are connected to each other through a bus 29, such as a system bus or a control bus, so as to be able to transmit and receive various kinds of information.

The controller 20 of the embodiment controls the overall operation of the image preservation system 8. The controller 20 comprises a central processing unit (CPU) 20A, a read only memory (ROM) 20B, and a random access memory (RAM) 20C. Various programs executed by the CPU 20A are stored in the ROM 20B in advance. The RAM 20C temporarily stores various kinds of data.

The storage unit 22 is a so-called database that stores the image data of the radiographic image in association with various kinds of information such as an imaging order or information relating to the subject. Specific examples of the storage unit 22 include a hard disk drive (HDD) and a solid state drive (SSD). The I/F unit 28 has a function of performing communication of various kinds of information with the console 6, the image processing apparatus 10, and the image interpretation apparatus 12 using wireless communication or wired communication.

Next, the configuration of the image processing apparatus 10 will be described.

The image processing apparatus 10 of the embodiment is an apparatus that performs desired image processing on the radiographic image. Specific examples of the image processing apparatus 10 include an image processing workstation.

Figure 3:
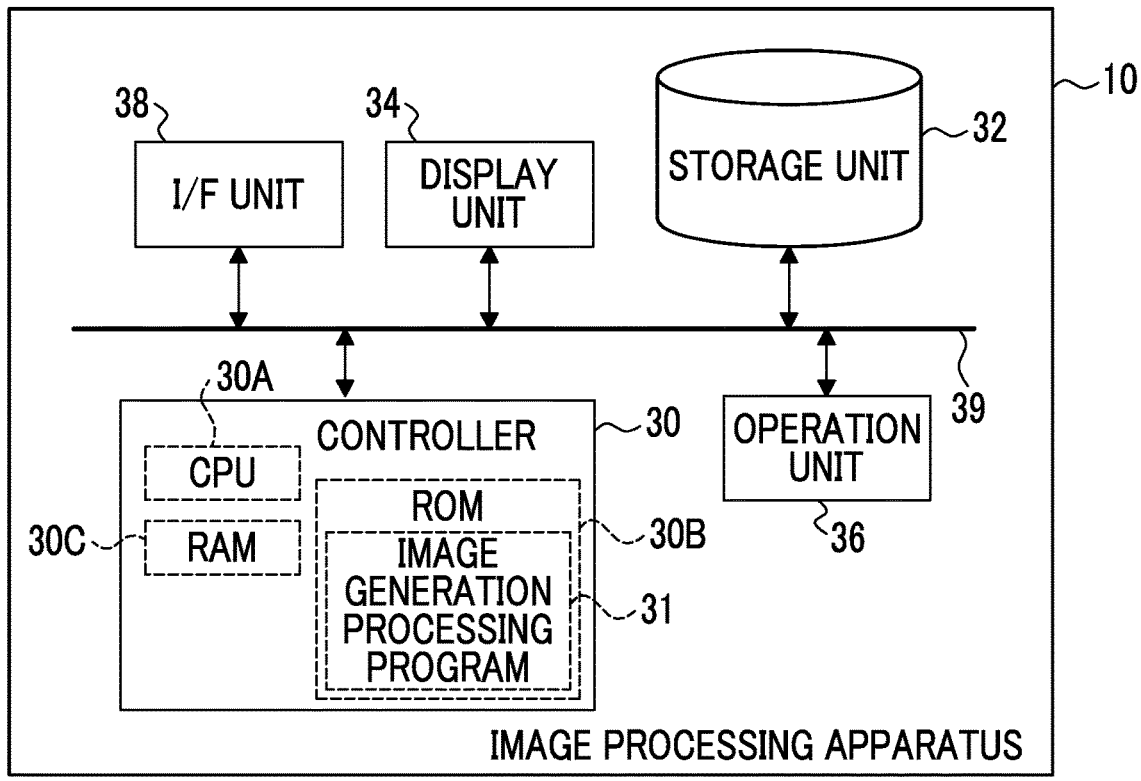
FIG. 3 is a block diagram illustrating an example of the configuration of an image processing apparatus of the first embodiment.

FIG. 3 is a block diagram illustrating an example of the image processing apparatus 10 of the embodiment. As illustrated in FIG. 3, the image processing apparatus 10 of the embodiment comprises a controller 30, a storage unit 32, a display unit 34, an operation unit 36, and an I/F unit 38. The controller 30, the storage unit 32, the display unit 34, the operation unit 36, and the I/F unit 38 are connected to each other through a bus 39, such as a system bus or a control bus, so as to be able to transmit and receive various kinds of information.

The controller 30 of the embodiment controls the overall operation of the image processing apparatus 10. The controller 30 comprises a CPU 30A, a ROM 30B, and a RAM 30C. Various programs including an image generation processing program 31 executed by the CPU 30A are stored in the ROM 30B in advance. The RAM 30C temporarily stores various kinds of data.

The image data of the radiographic image and various other kinds of information are stored in the storage unit 32. Specific examples of the storage unit 32 include an HDD, an SSD, and the like. The operation unit 36 is used by the user to input an instruction or the like relating to image processing that is performed on the radiographic image. The operation unit 36 is not particularly limited, and for example, various switches, a touch panel, a touch pen, a mouse, and the like are exemplified. The display unit 34 displays various kinds of information including the radiographic image. In addition, the display unit 34 and the operation unit 36 may be integrated into a touch panel display. The I/F unit 38 performs communication of various kinds of information including the image data of the radiographic image, with the console 6, the image preservation system 8, and the image interpretation apparatus 12 using wireless communication or wired communication.

Next, the configuration of the image interpretation apparatus 12 will be described.

The image interpretation apparatus 12 of the embodiment is an apparatus for the interpreter such as a doctor to interpret the radiographic image captured by the radiography system 2. Specific examples of the image interpretation apparatus 12 include a so-called viewer.

Figure 4:
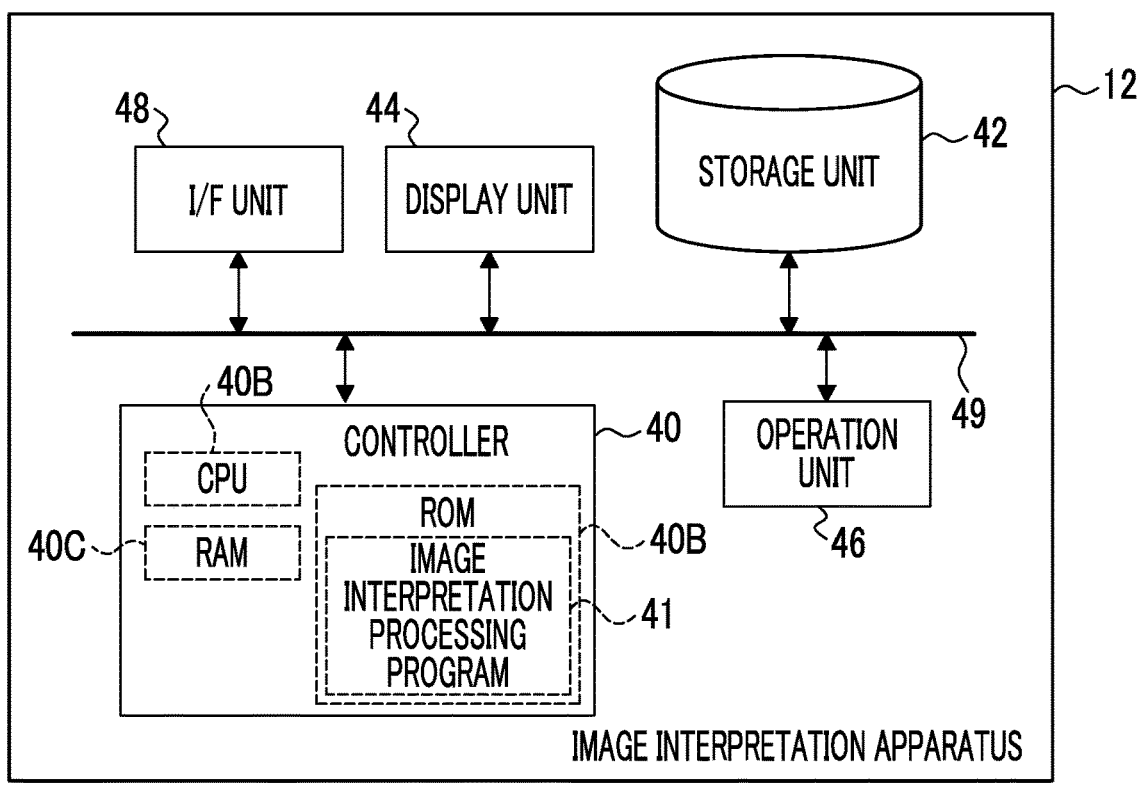
FIG. 4 is a block diagram illustrating an example of the configuration of an image interpretation apparatus of the first embodiment.

FIG. 4 is a block diagram illustrating an example of the image interpretation apparatus 12 of the embodiment. As illustrated in FIG. 4, the image interpretation apparatus 12 of the embodiment comprises a controller 40, a storage unit 42, a display unit 44, an operation unit 46, and an I/F unit 48. The controller 40, the storage unit 42, the display unit 44, the operation unit 46, and the I/F unit 48 are connected to each other through a bus 49, such as a system bus or a control bus, so as to be able to transmit and receive various kinds of information.

The controller 40 of the embodiment controls the overall operation of the image interpretation apparatus 12. The controller 40 comprises a CPU 40A, a ROM 40B, and a RAM 40C. Various programs including an image interpretation processing program 41 executed by the CPU 40A are stored in the ROM 40B in advance. The RAM 40C temporarily stores various kinds of data. The image interpretation processing program 41 and the image generation processing program 31 of the embodiment are examples of the image processing program of the present disclosure.

The image data of the radiographic image and various other kinds of information are stored in the storage unit 42. Specific examples of the storage unit 42 include an HDD, an SSD, and the like. The operation unit 46 is used by the interpreter to input an instruction or the like relating to the interpretation of the radiographic image. The operation unit 46 is not particularly limited, and for example, various switches, a touch panel, a touch pen, a mouse, and the like are exemplified. The display unit 44 displays various kinds of information including the radiographic image. In addition, the display unit 44 and the operation unit 46 may be integrated into a touch panel display. The I/F unit 48 performs communication of various kinds of information including the image data of the radiographic image, with the image preservation system 8 and the image processing apparatus 10 using wireless communication or wired communication.

Figure 5:
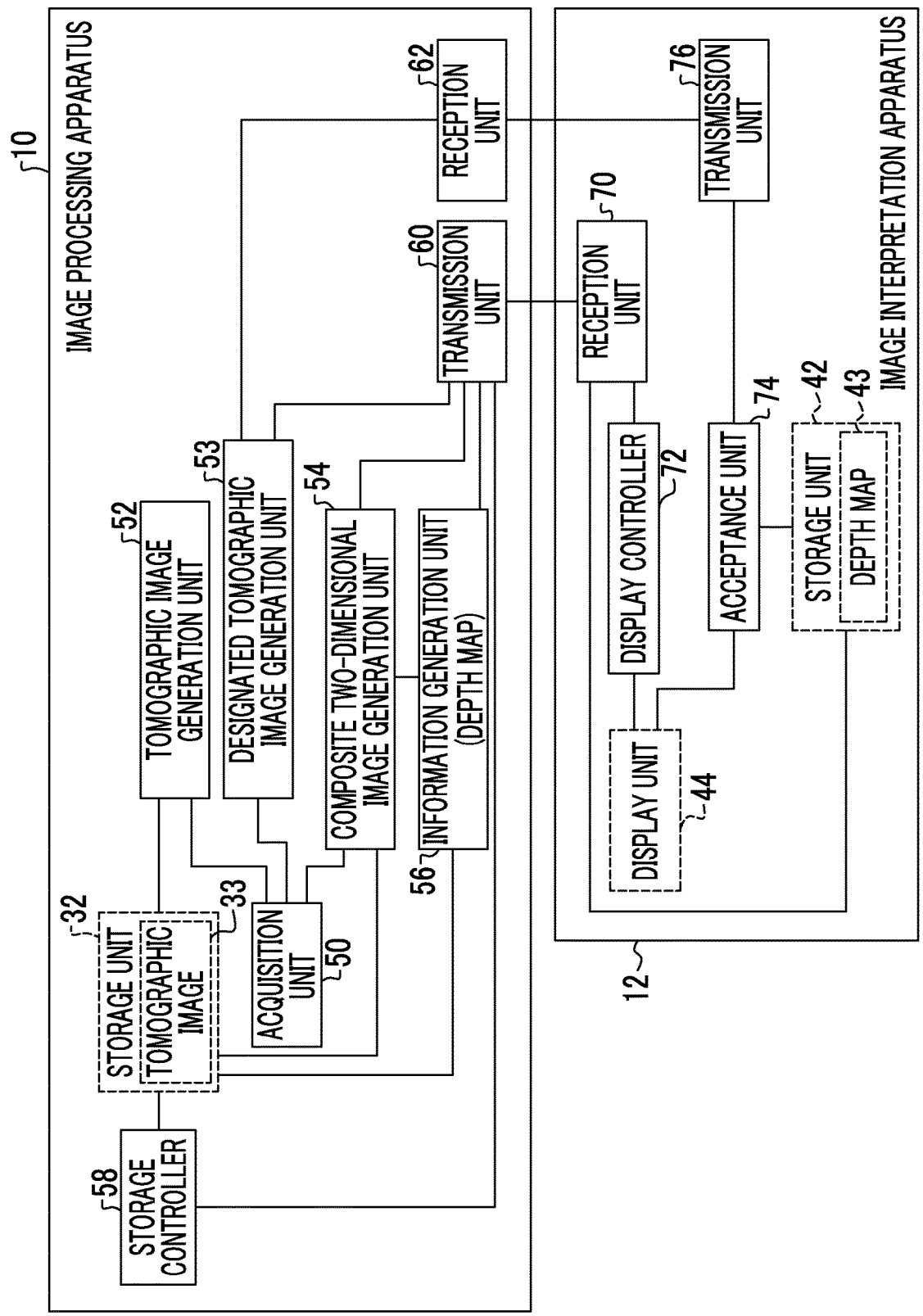
FIG. 5 is a functional block diagram illustrating an example of functions of the image processing apparatus and the image interpretation apparatus of the first embodiment.

FIG. 5 is a functional block diagram illustrating an example of the configurations of the image processing apparatus 10 and the image interpretation apparatus 12 of the embodiment. As illustrated in FIG. 5, the image processing apparatus 10 of the embodiment comprises an acquisition unit 50, a tomographic image generation unit 52, a designated tomographic image generation unit 53, a composite two-dimensional image generation unit 54, an information generation unit 56, a storage controller 58, a transmission unit 60, and a reception unit 62.

For example, in the image processing apparatus 10 of the embodiment, the CPU 30A of the controller 30 executes the image generation processing program 31 stored in the ROM 30B so that the controller 30 functions as each of the acquisition unit 50, the tomographic image generation unit 52, the designated tomographic image generation unit 53, the composite two-dimensional image generation unit 54, the information generation unit 56, the storage controller 58, the transmission unit 60, and the reception unit 62.

The acquisition unit 50 acquires a plurality of projection images captured by the mammography apparatus 4, and outputs the plurality of acquired projection images to the tomographic image generation unit 52, the designated tomographic image generation unit 53, and the composite two-dimensional image generation unit 54. The acquisition source from which the acquisition unit 50 acquires a plurality of projection images is not limited, and for example, the image preservation system 8 or the console 6 may be the acquisition source, or in a case where images are stored in the storage unit 32 in advance, the storage unit 32 may be the acquisition source.

The tomographic image generation unit 52 reconstructs all or some of the plurality of projection images input from the acquisition unit 50 to generate a tomographic image. The tomographic image generation unit 52 generates a plurality of tomographic images (hereinafter, referred to as a "tomographic image 33") in each of a plurality of tomographic planes of the breast. The tomographic image 33 generated by the tomographic image generation unit 52 is temporarily stored in the storage unit 32.

On the other hand, in a case where the reception unit 62 has received depth information, the designated tomographic image generation unit 53 generates a tomographic image in the tomographic plane of the breast specified by the depth information, as a designated tomographic image. The size or the like of the designated tomographic image generated by the designated tomographic image generation unit 53 is optional. For example, the designated tomographic image may be used as a tomographic image of a portion corresponding to a region, which is designated by the interpreter (hereinafter, referred to as a "designated region") in the image interpretation apparatus 12, in the specified tomographic plane. In this case, the designated tomographic image generation unit 53 may not generate a tomographic image of a portion corresponding to a region other than the designated region in the specified tomographic plane. In other words, an aspect of generating a tomographic image of only a partial region of the tomographic planes of the entire breast may be adopted.

For example, the designated tomographic image may be used as a tomographic image of a portion corresponding to a region in a predetermined range including the designated region. In this case, in a case where the designated region is a region including a part of a region of interest, a tomographic image of a region including the designated region and the entire region of interest can be used as the designated tomographic image.

For example, the designated tomographic image may be a tomographic image having a size including the image of the entire breast, or may be a tomographic image in the same range (size) as the tomographic image 33 generated by the tomographic image generation unit 52.

What kind of tomographic image, for example, which size tomographic image, is used as the designated tomographic image may be determined in advance, or can be set and changed by the interpreter.

In this manner, the tomographic image generation unit 52 generates a plurality of tomographic images respectively corresponding to all of a plurality of tomographic planes (depths) of the breast, and the designated tomographic image generation unit 53 generates a tomographic image in a specific tomographic plane (depth) as the designated tomographic image.

The method in which each of the tomographic image generation unit 52 and the designated tomographic image generation unit 53 generates a tomographic image from a plurality of projection images is not particularly limited, and for example, a known method such as a back projection method such as a filtered back projection (FBP) method and a simple back projection method, or a shift addition method can be used.

The composite two-dimensional image generation unit 54 generates a composite two-dimensional image from a plurality of radiographic images selected from among a plurality of projection images and a plurality of tomographic images. The composite two-dimensional image generated by the composite two-dimensional image generation unit 54 is output to the information generation unit 56. A plurality of radiographic images used in the generation of the composite two-dimensional image by the composite two-dimensional image generation unit 54 are not particularly limited, and may be determined in advance or may be selected by the interpreter or the like.

The method in which the composite two-dimensional image generation unit 54 generates the composite two-dimensional image is not particularly limited, and a known method can be used. As an example, the composite two-dimensional image generation unit 54 of the embodiment uses a method disclosed in U.S. Pat. No. 8,983,156B. U.S. Pat. No. 8,983,156B discloses a technique of generating a composite two-dimensional image in which a lesion or the like detected from a tomographic image is reflected, by blending (composing) a region of interest (ROI) detected from the tomographic image with a two-dimensional image to generate a composite two-dimensional image. The method of detecting a region of interest from a tomographic image is not particularly limited, and for example, a method of extracting a specific structure representing a region of interest from a tomographic image using an algorithm of a known computer aided diagnosis (CAD) (hereinafter, referred to as CAD) is exemplified. In the algorithm by the CAD, it is preferable to derive a probability (for example, likelihood) representing that a pixel in the tomographic image is a region of interest, and to detect the pixel as a pixel constituting an image of the region of interest in a case where the probability is equal to or greater than a predetermined threshold value. Further, a method of extracting a region of interest from a tomographic image by filtering processing using filters for extracting a region of interest or the like may be used.

As the method in which the composite two-dimensional image generation unit 54 generates the composite two-dimensional image, a method of generating a composite two-dimensional image by using a minimum intensity projection method or projecting a plurality of tomographic images or at least one of a plurality of tomographic images and at least one of a plurality of projection images in the depth direction in which the tomographic planes of the breast are lined up, disclosed in 2014-128716A may be used. Further, for example, a method of generating a composite two-dimensional image by reconstructing a plurality of tomographic images or at least one of a plurality of tomographic images and at least one of a plurality of projection images using any method of a filtered back projection method, a maximum likelihood reconstruction method, an iterative reconstruction method, a reconstruction method using the algebraic method, and a 3D reconstruction method, disclosed in JP6208731B may be used.

The information generation unit 56 generates a depth map 43 representing a correspondence relationship between a position in the composite two-dimensional image and the depth of the tomographic plane corresponding to the position. The depth map 43 of the embodiment is an example of correspondence relationship information of the present disclosure.

Figure 6:
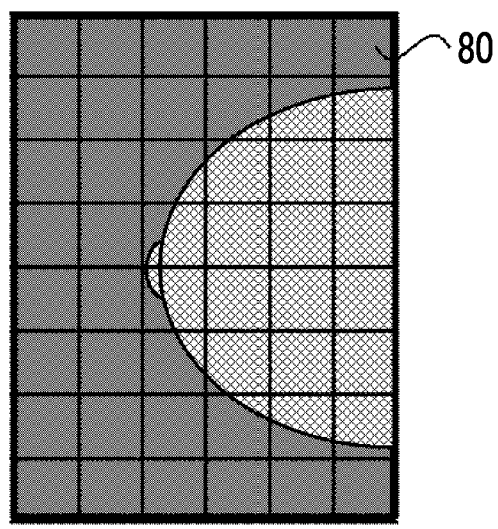
FIG. 6 is a diagram illustrating an example of a depth map.

The method in which the information generation unit 56 generates the depth map 43 is not particularly limited, and a known method can be used. For example, a method disclosed in WO2014/203531A may be used. In the method disclosed in WO2014/203531A, a composite two-dimensional image is divided into a plurality of local regions and a correlation between a plurality of tomographic images and the regions obtained by the division is obtained. For example, as illustrated in FIG. 6, a composite two-dimensional image 80 is divided into 48 (6×8) local regions, and a correlation with a plurality of tomographic images is derived for each of the divided regions. Then, the depth map 43 is created by associating a depth of a tomographic plane of a tomographic image including a region with the highest correlation from a reference position, with a position of each region in the composite two-dimensional image 80. For example, the reference position may be a contact surface between the breast and a pressing plate (not illustrated) which presses the breast in a case where the breast is imaged by the mammography apparatus 4. Here, the position of the tomographic plane in a case of generating the tomographic image is known. Thus, in the example illustrated in FIG. 6, it is possible to specify the position of the tomographic plane corresponding to each of 48 local regions in the composite two-dimensional image 80 by referring to the depth map 43. In generation of the depth map 43, the number of local regions and the shape of the region are not particularly limited. Both the number of local regions and the shape of the region may be determined in advance according to the size of the composite two-dimensional image 80, a desired accuracy, and the like, and may be set by the interpreter or the like.

The transmission unit 60 transmits the composite two-dimensional image generated by the composite two-dimensional image generation unit 54, the depth map 43 generated by the information generation unit 56, and the designated tomographic image generated by the designated tomographic image generation unit 53 to the image interpretation apparatus 12.

The reception unit 62 receives depth information, which will be described in detail below, from the image interpretation apparatus 12, and outputs the depth information to the designated tomographic image generation unit 53.

In a case where the composite two-dimensional image generation unit 54 has generated the composite two-dimensional image and the information generation unit 56 has generated the depth map 43, the storage controller 58 performs control of deleting the tomographic image 33 from the storage unit 32. For example, in a case where the transmission unit 60 transmits the composite two-dimensional image and the depth map 43 to the image interpretation apparatus 12, the storage controller 58 of the embodiment deletes the tomographic image 33 from the storage unit 32.

On the other hand, as illustrated in FIG. 5, the image interpretation apparatus 12 of the embodiment comprises a reception unit 70, a display controller 72, an acceptance unit 74, and a transmission unit 76.

For example, in the image interpretation apparatus 12 of the embodiment, the CPU 40A of the controller 40 executes the image interpretation processing program 41 stored in the ROM 40B so that the controller 40 functions as the reception unit 70, the display controller 72, the acceptance unit 74, and the transmission unit 76.

The reception unit 70 receives the composite two-dimensional image, the depth map 43, and the designated tomographic image which are transmitted from the image processing apparatus 10. The composite two-dimensional image and the designated tomographic image received by the reception unit 70 are output to the display controller 72. Further, the depth map 43 received by the reception unit 70 is stored in the storage unit 42.

The display controller 72 performs control of causing the display unit 44 to display each of the composite two-dimensional image and the designated tomographic image. The acceptance unit 74 accepts region information representing a designated region that is designated with respect to the composite two-dimensional image, which is caused to be displayed on the display unit 44 by the display controller 72, by the interpreter using the operation unit 46, and outputs the accepted region information to the transmission unit 76. The transmission unit 76 transmits the region information to the image processing apparatus 10.

Next, the operation of the image processing system 3 of the embodiment will be described with reference to the drawings.

In the image processing system 3 of the embodiment, for example, in a case where the interpreter gives an instruction to perform the interpretation of the radiographic image using the operation unit 46 in the image interpretation apparatus 12, the image processing apparatus 10 executes the image generation processing and the image interpretation apparatus 12 executes image interpretation processing.

Figure 7:
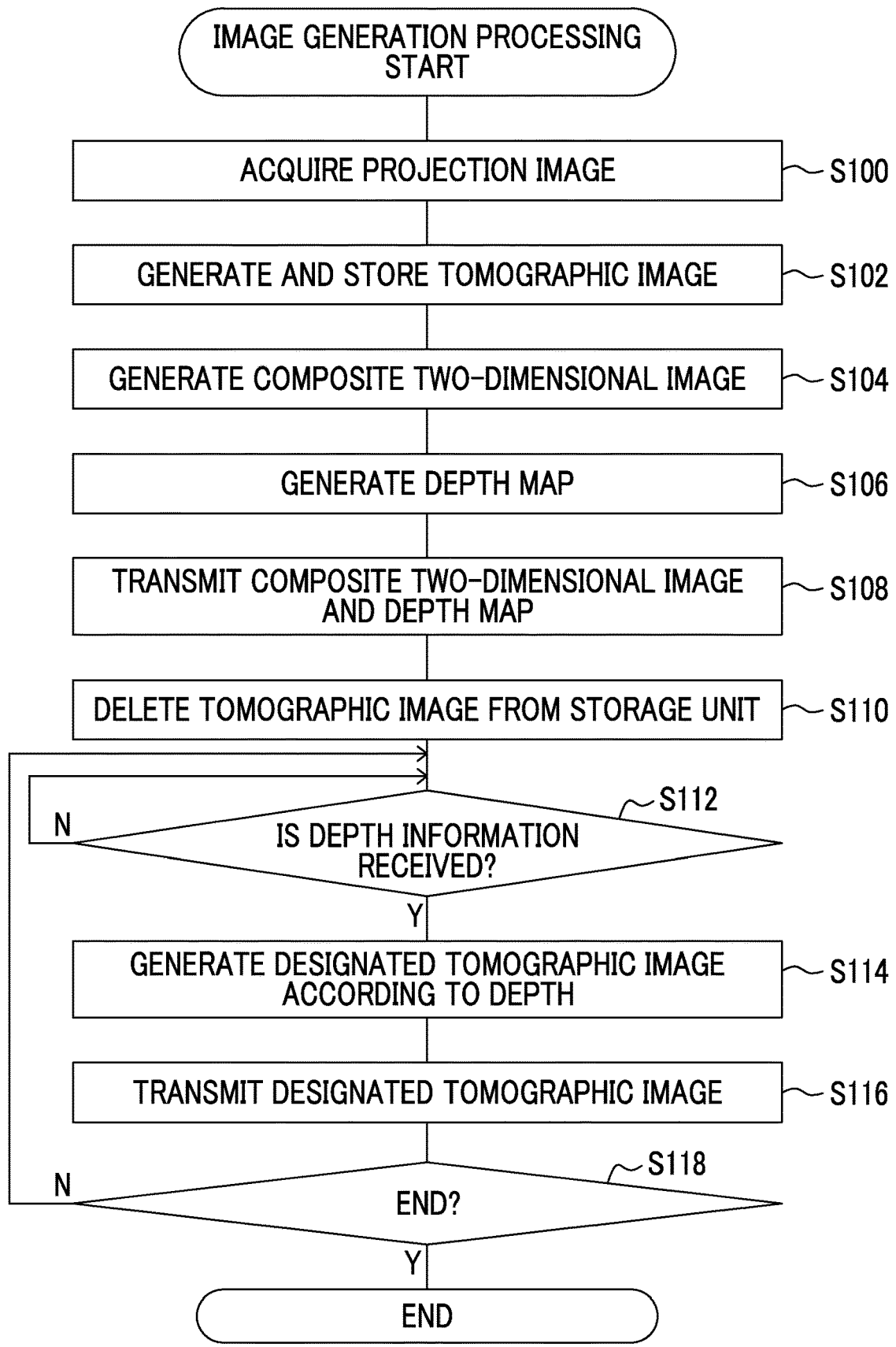
FIG. 7 is a flowchart illustrating an example of the flow of image generation processing of an image processing apparatus of the first embodiment.

First, the image generation processing executed by the image processing apparatus 10 will be described. In the image processing apparatus 10, in a case where an instruction to perform image interpretation is given, the CPU 30A of the controller 30 executes the image generation processing program 31 stored in the ROM 30B to execute the image generation processing of which an example is illustrated in FIG. 7. FIG. 7 is a flowchart illustrating an example of the flow of image generation processing of the image processing apparatus 10 of the embodiment.

In the image generation processing illustrated in FIG. 7, in step S100, the acquisition unit 50 acquires a plurality of projection images corresponding to an image interpretation target according to the user's instruction as described above.

In step S102, the tomographic image generation unit 52 reconstructs all or some of the plurality of projection images to generate a plurality of tomographic images 33 as described above. In step S104, the composite two-dimensional image generation unit 54 generates a composite two-dimensional image from a plurality of radiographic images selected from among the plurality of projection images and the plurality of tomographic images 33 as described above. In step S106, the information generation unit 56 generates the depth map 43 from the composite two-dimensional image and the tomographic image 33 as described above.

Is step S108, the transmission unit 60 transmits the composite two-dimensional image generated in step S104 and the depth map 43 generated in step S106 to the image interpretation apparatus 12. As will be described in detail below, in the image interpretation apparatus 12 that has received the composite two-dimensional image and the depth map 43, the display unit 44 displays the composite two-dimensional image (refer to FIG. 9A).

In step S110, the storage controller 58 deletes the tomographic image 33 from the storage unit 32 as described above.

In step S112, the reception unit 62 determines whether the depth information is received as described above. The determination of step S112 is negative until the depth information is received from the image interpretation apparatus 12. On the other hand, the determination of step S112 is affirmative in a case where the depth information is received from the image interpretation apparatus 12, and the processing proceeds to step S114.

In step S114, the designated tomographic image generation unit 53 generates a tomographic image in a tomographic plane at a depth represented by the depth information, as the designated tomographic image. In step S116, the transmission unit 60 outputs the generated designated tomographic image to the image interpretation apparatus 12.

In step S118, the reception unit 62 determines whether the present image generation processing is to be ended. For example, in the embodiment, in a case where the display of the radiographic image is ended in the image interpretation apparatus 12, in other words, in a case where the interpreter ends the image interpretation in the image interpretation apparatus 12, the reception unit 62 receives an end instruction (refer to step S218 of FIG. 8) transmitted from the image interpretation apparatus 12. Therefore, the determination of step S118 is negative until the reception unit 62 receives the end instruction, the processing returns to step S112, and the processing of steps S114 to S118 is repeated. On the other hand, in a case where the reception unit 62 receives the end instruction, the determination of step S118 is affirmative, and the present image generation processing is ended.

Figure 8:
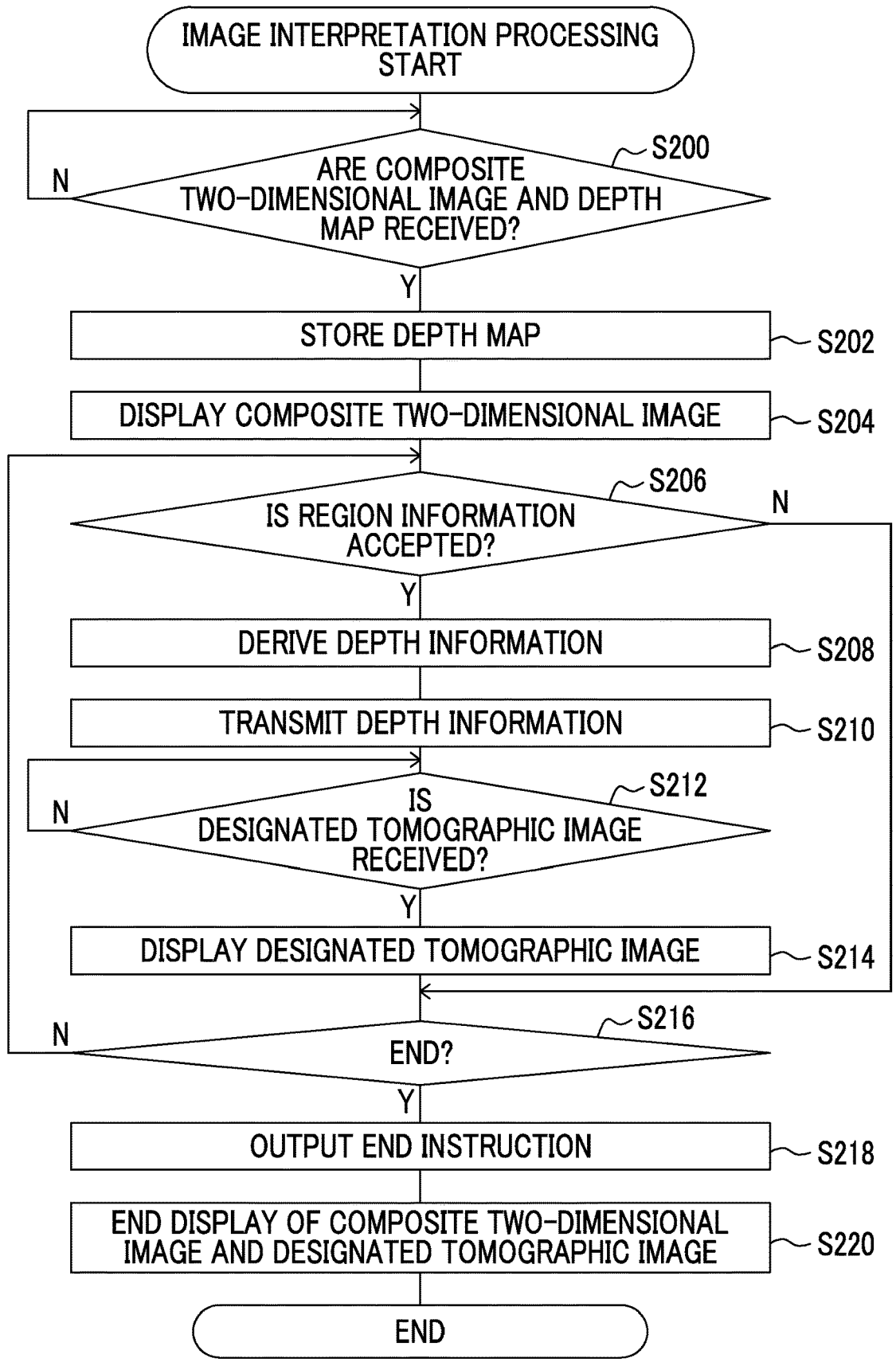
FIG. 8 is a flowchart illustrating an example of the flow of image generation processing of an image interpretation apparatus of the first embodiment.

Next, the image interpretation processing executed by the image interpretation apparatus 12 will be described. In the image interpretation apparatus 12, in a case where an instruction to perform image interpretation is given, the CPU 40A of the controller 40 executes the image interpretation processing program 41 stored in the ROM 40B to execute the image interpretation processing of which an example is illustrated in FIG. 8. FIG. 8 is a flowchart illustrating an example of the flow of image interpretation processing of the image interpretation apparatus 12 of the embodiment.

In the image interpretation processing illustrated in FIG. 8, in step S200, the reception unit 70 determines whether the composite two-dimensional image and the depth map 43 are received. The determination of step S200 is negative until the reception unit 70 receives the composite two-dimensional image and the depth map 43 which are transmitted from the image processing apparatus 10 by the processing of step S108 in the image generation processing (refer to FIG. 7). On the other hand, in a case where the composite two-dimensional image and the depth map 43 are received from the image processing apparatus 10, the determination of step S200 is affirmative, and the processing proceeds to step S202. In step S202, the reception unit 70 causes the received depth map 43 to be stored in the storage unit 42.

Figure 9A:
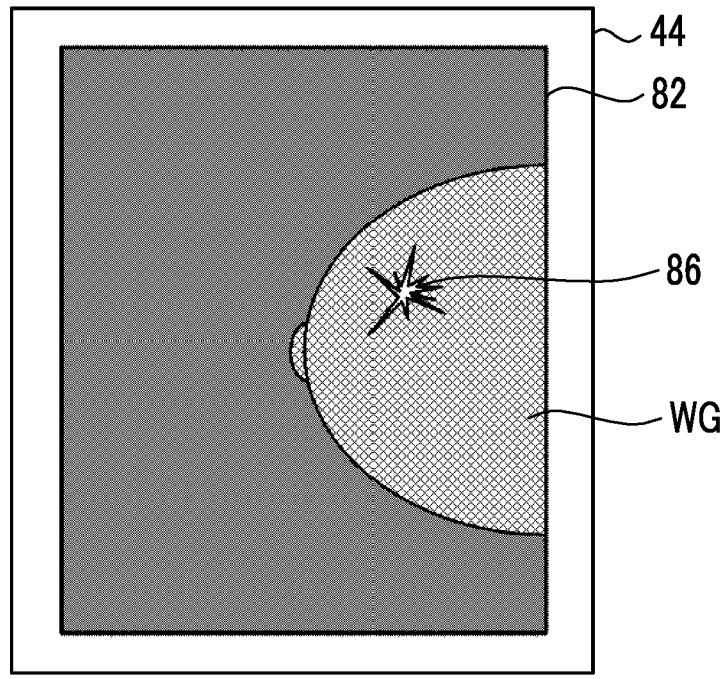
FIG. 9A is a diagram illustrating an example of a display form of a composite two-dimensional image.

In step S204, the display controller 72 causes the display unit 44 to display the composite two-dimensional image. FIG. 9A illustrates an example of a display form of a composite two-dimensional image 82 displayed on the display unit 44. In the composite two-dimensional image 82 illustrated in FIG. 9A, a breast image WG including a region of interest 86 is included.

The interpreter designates a region (above-described designated region), in which a tomographic image is desired to be referred to, with respect to the composite two-dimensional image 82 using the operation unit 46. The method in which the interpreter designates the designated region is not particularly limited.

Figure 9B:
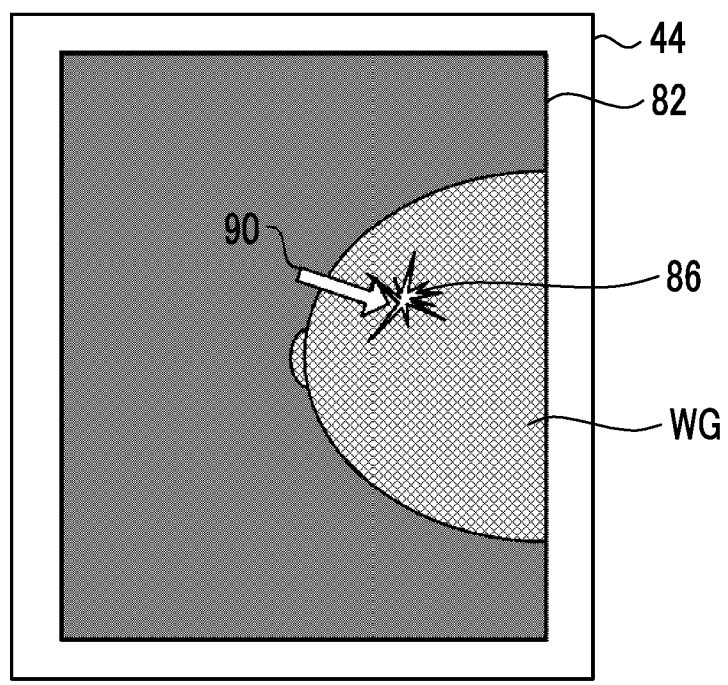
FIG. 9B is a diagram illustrating an example of designation of a region by an interpreter.

For example, FIG. 9B illustrates an example of a case in which the region of interest 86 included in the breast image WG of the composite two-dimensional image 82 illustrated in FIG. 9A is designated with an arrow icon 90 that appears by the interpreter operating the operation unit 46. For example, in the embodiment, in a case where the region of interest 86 is designated with the icon 90 as illustrated in FIG. 9B, the acceptance unit 74 accepts region information that specifies a rectangular region inscribed in the region of interest 86 as the designated region.

Figure 9C:
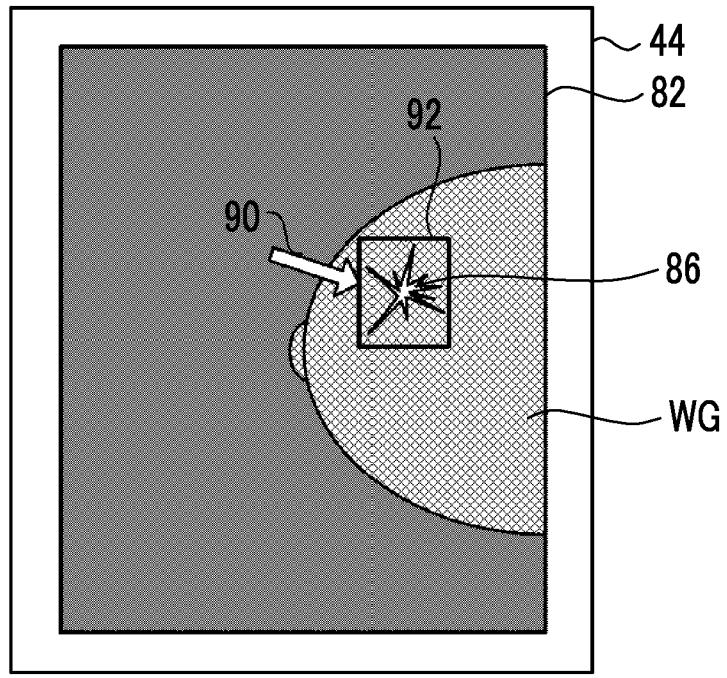
FIG. 9C is a diagram illustrating another example of designation of a region by an interpreter.

As illustrated in FIG. 9C, in a case where the interpreter moves the icon 90 on the composite two-dimensional image 82, the acceptance unit 74 accepts region information that specifies a region surrounded by a trajectory 92 of the icon 90 as the designated region. In this case, it is preferable to add a line image representing the trajectory 92 to the composite two-dimensional image 82.

In a case where the designated region is designated by the interpreter in this manner, the acceptance unit 74 accepts region information representing the designated region. Therefore, in step S206, the acceptance unit 74 determines whether the region information is accepted. In a case where the acceptance unit 74 has not accepted the region information yet, the determination of step S206 is negative, and the processing proceeds to step S216. On the other hand, in a case where the acceptance unit 74 has accepted the region information, the determination of step S206 is affirmative, and the processing proceeds to step S208.

In step S208, the acceptance unit 74 refers to the depth map 43 and derives the depth information representing the depth which is associated with the position on the composite two-dimensional image specified by the accepted region information.

In step S210, the transmission unit 76 transmits the depth information derived by the acceptance unit 74 to the image processing apparatus 10. As described above, the image processing apparatus 10 generates the designated tomographic image according to the depth represented by the depth information by the processing of steps S114 to S116 in the image generation processing (refer to FIG. 7), and outputs the designated tomographic image to the image interpretation apparatus 12. Therefore, in step S212, the reception unit 70 determines whether the designated tomographic image is received. The determination of step S212 is negative until the reception unit 70 receives the designated tomographic image. On the other hand, the determination of step S212 is affirmative in a case where the reception unit 70 receives the designated tomographic image, and the processing proceeds to step S214.

Figure 10A:
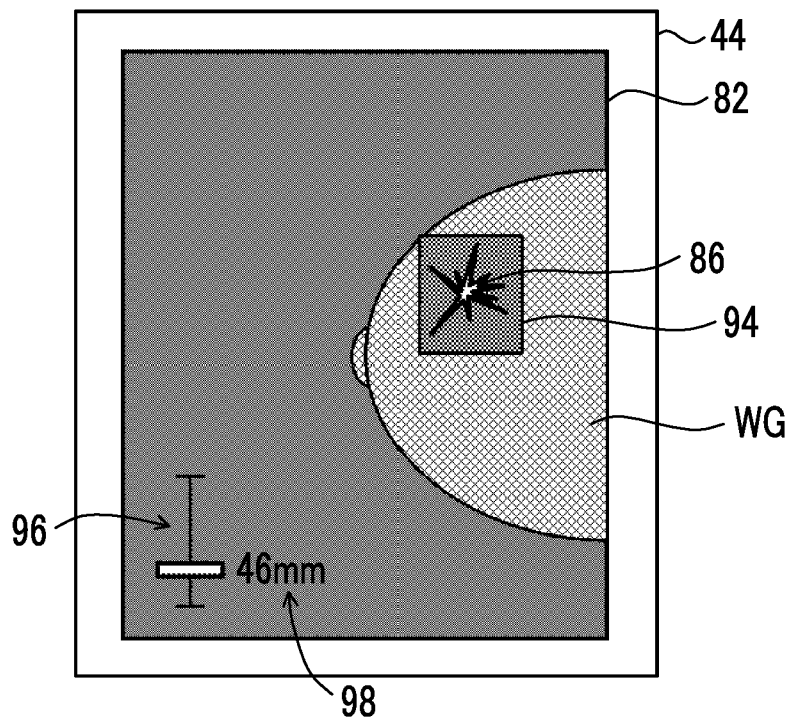
FIG. 10A is a diagram illustrating an example of a display form of a composite two-dimensional image and a designated tomographic image.

In step S214, the display controller 72 causes the display unit 44 to display the designated tomographic image. The display form in which the display controller 72 causes the display unit 44 to display the designated tomographic image is not particularly limited. For example, as illustrated in FIG. 10A, a form in which a designated tomographic image 94 is displayed on the display unit 44 in a state of being superimposed on the designated region of the composite two-dimensional image 82 may be used. In this case, a form in which the composite two-dimensional image 82 and the designated tomographic image 94 are entirely superimposed on each other may be used, or a form in which the composite two-dimensional image 82 and the designated tomographic image 94 are partially superimposed on each other may be used. In the display form illustrated in FIG. 10A, by displaying a scale 96 representing the position of the tomographic plane of the designated tomographic image 94 in the depth direction, and a numerical value 98 representing the depth of the tomographic plane, the position of the region of interest 86 is easily recognized.

Figure 10B:
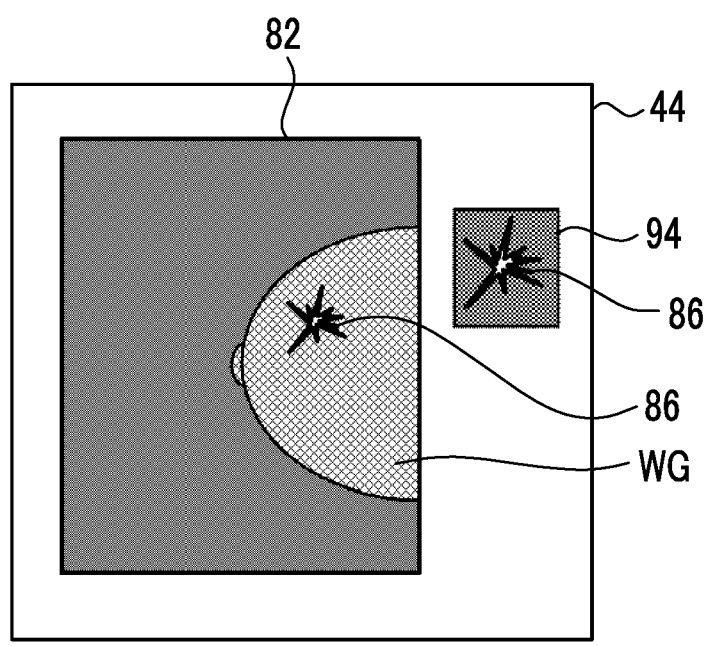
FIG. 10B is a diagram illustrating another example of a display form of a composite two-dimensional image and a designated tomographic image.

For example, as illustrated in FIG. 10B, a form in which the composite two-dimensional image 82 and the designated tomographic image 94 are displayed side by side on the display unit 44 may be used. Further, as illustrated in FIG. 10B, by using a form in which the designated tomographic image 94 is displayed to be enlarged compared to the composite two-dimensional image 82, the image interpretation of the region of interest 86 can be easily performed.

In step S216, the transmission unit 76 determines whether the image interpretation is to be ended. For example, in the embodiment, since the interpreter gives an instruction to end the processing using the operation unit 46 in case of ending the image interpretation, the transmission unit 76 determines whether the processing is to be ended by determining whether an instruction to end the image interpretation is given. In a case where the image interpretation is not to be ended, in other words, in a case where an instruction to end the image interpretation is not given, the determination of step S216 is negative, and the processing returns to step S206, and the processing of steps S208 to S214 is repeated. On the other hand, in a case where the image interpretation is to be ended, in other words, in a case where an instruction to end the image interpretation is given, the determination of step S216 is affirmative, and the processing proceeds to step S218.

In step S218, the transmission unit 76 transmits the end instruction representing that the image interpretation is to be ended to the image processing apparatus 10. In step S220, the display controller 72 ends the display of the composite two-dimensional image 82 and the designated tomographic image 94 on the display unit 44, and then the present image interpretation processing is ended.

By storing the generated composite two-dimensional image and depth map 43 in an association manner in the image preservation system 8 or the like, from the next time, in a case where interpretation of the composite two-dimensional image is performed in the image interpretation apparatus 12, it is possible to skip the processing of steps S100 to S110 in the image generation processing. In this case, in step S200 in the image interpretation processing, the reception unit 70 of the image interpretation apparatus 12 may receive the composite two-dimensional image and the depth map 43 from the image preservation system 8 or the like.

Second Embodiment

An aspect in which the image processing apparatus 10 generates the designated tomographic image has been described in the first embodiment, but in the second embodiment, an aspect in which the image interpretation apparatus 12 generates the designated tomographic image in the image processing system 3 will be described.

Figure 11:
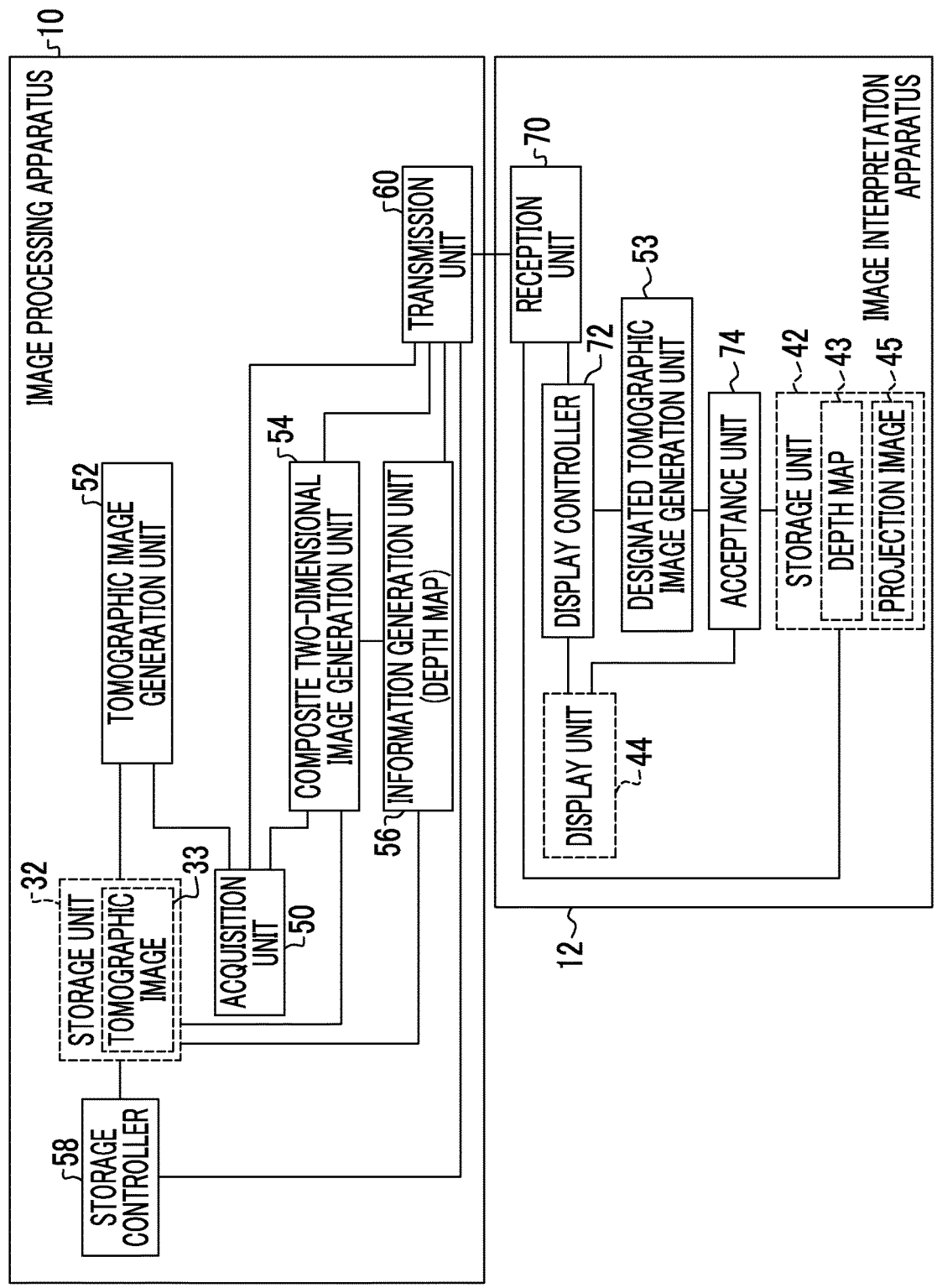
FIG. 11 is a functional block diagram illustrating an example of functions of an image processing apparatus and an image interpretation apparatus of a second embodiment.

FIG. 11 is a functional block diagram illustrating an example of the configurations of the image processing apparatus 10 and the image interpretation apparatus 12 of the embodiment. As illustrated in FIG. 11, the image processing apparatus 10 of the second embodiment is different from the image processing apparatus 10 of the first embodiment (refer to FIG. 5) in that the reception unit 62 and the designated tomographic image generation unit 53 are not provided.

Further, the image processing apparatus 10 of the second embodiment is different from the image processing apparatus 10 of the first embodiment in that the transmission unit 60 transmits a plurality of projection images acquired by the acquisition unit 50 to the image interpretation apparatus 12.

On the other hand, as illustrated in FIG. 11, the image interpretation apparatus 12 of the second embodiment is different from the image interpretation apparatus 12 of the first embodiment (refer to FIG. 5) in that the designated tomographic image generation unit 53 is provided and the transmission unit 76 is not provided.

Further, the reception unit 70 of the image interpretation apparatus 12 of the second embodiment is different from the reception unit 70 of the first embodiment in that the reception unit 70 receives a plurality of projection images 45 from the image processing apparatus 10 and causes the projection images 45 to be stored in the storage unit 42.

Each unit in the image processing apparatus 10 and the image interpretation apparatus 12 other than the transmission unit 60 of the image processing apparatus 10 and the reception unit 70 of the image interpretation apparatus 12 has the same function as that of the first embodiment even in a case where the apparatus in which the unit is provided is different.

Next, the operation of the image processing system 3 of the embodiment will be described.

Figure 12:
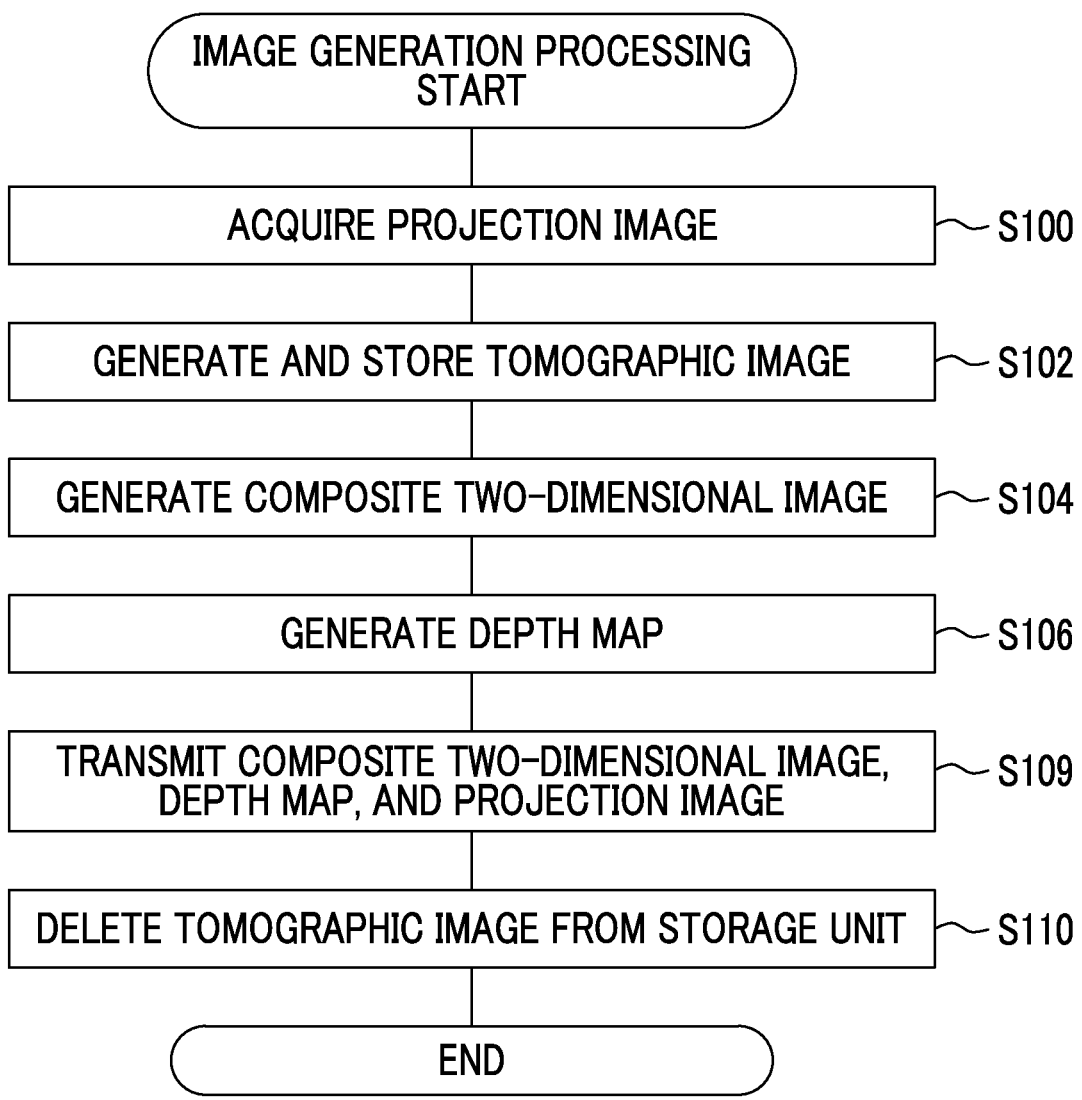
FIG. 12 is a flowchart illustrating an example of the flow of image generation processing of an image processing apparatus of the second embodiment.

FIG. 12 is a flowchart illustrating an example of the flow of image generation processing of the image processing apparatus 10 of the embodiment. The image generation processing illustrated in FIG. 12 is different from the image generation processing of the first embodiment (refer to FIG. 7) in that processing of step S109 is provided instead of the processing of step S108 and the processing of steps S112 to S118 is not provided.

As illustrated in FIG. 12, in step S109, the transmission unit 60 transmits the composite two-dimensional image, the depth map 43, and the projection image 45 to the image interpretation apparatus 12. As described above, the transmission unit 60 of the embodiment transmits a plurality of projection images required for generating the designated tomographic image to the image interpretation apparatus 12.

As illustrated in FIG. 12, in the image generation processing of the embodiment, in a case where the storage controller 58 deletes the tomographic image 33 from the storage unit 32 in step S110, the present image generation processing is ended.

Figure 13:
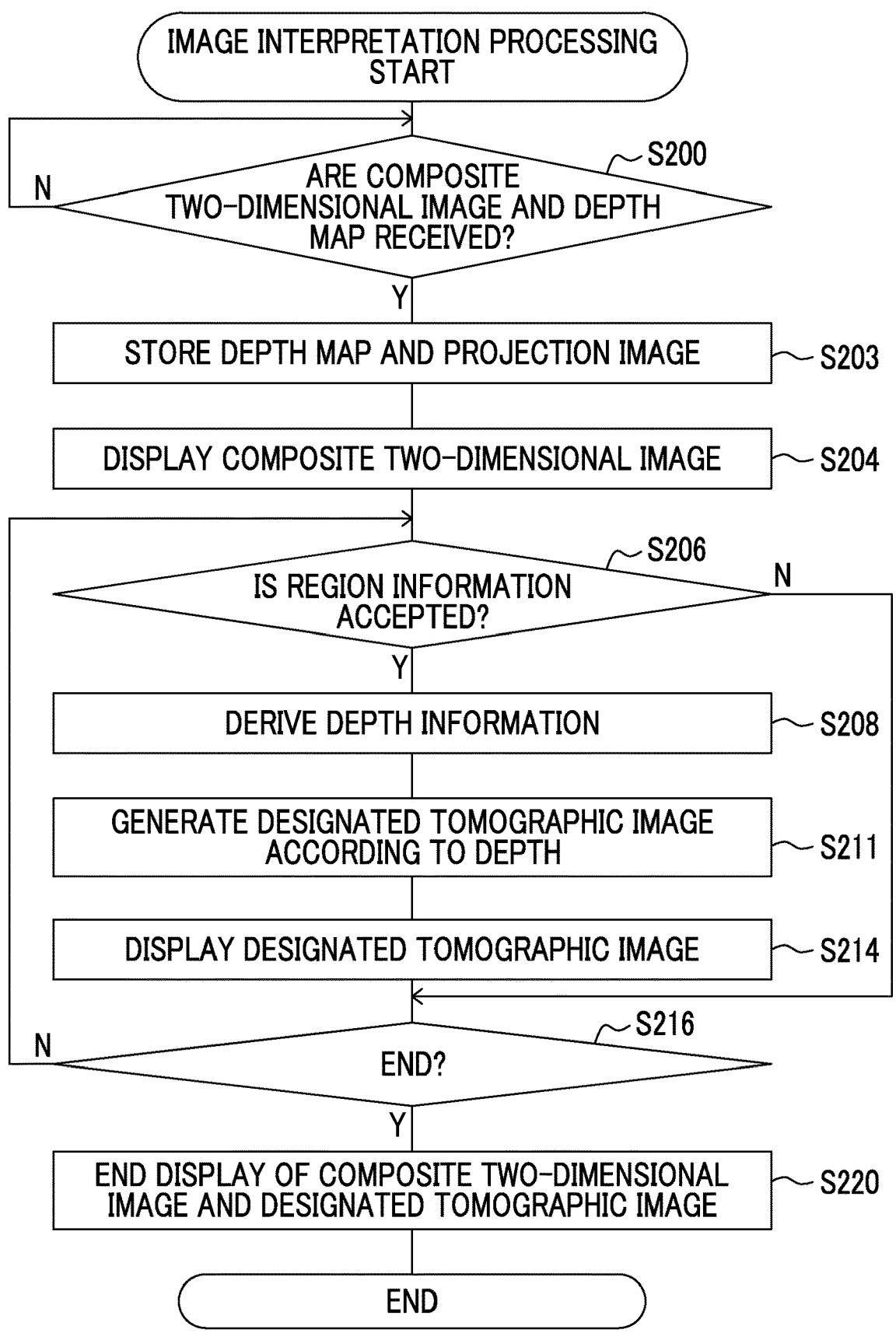
FIG. 13 is a flowchart illustrating an example of the flow of image generation processing of an image interpretation apparatus of the second embodiment.

On the other hand, FIG. 13 is a flowchart illustrating an example of the flow of image interpretation processing of the image interpretation apparatus 12 of the embodiment. The image interpretation processing illustrated in FIG. 13 is different from the image interpretation processing of the first embodiment (refer to FIG. 8) in that processing of step S203 is provided instead of the processing of step S202, processing of step S211 is provided instead of the processing of step S210 and step S212, and the processing of step S218 is not provided.

As illustrated in FIG. 13, in step S203, the reception unit 70 causes the depth map 43 and the projection image 45 to be stored in the storage unit 42.

As illustrated in FIG. 13, in a case where the depth information is derived in step S208, in step S211, the tomographic image generation unit 52 generates a tomographic image in a tomographic plane at a depth represented by the depth information, as the designated tomographic image, similarly to step S114 of the image generation processing of the first embodiment (refer to FIG. 7), and the processing proceeds to step S214.

Further, as illustrated in FIG. 13, in a case where an instruction to end the image interpretation is given so that the determination of step S216 is affirmative, the processing proceeds to step S220.

In the image processing system 3 of the embodiment, since the plurality of projection images 45, which are used for the image interpretation apparatus 12 to generate the designated tomographic image, are received and stored, the image interpretation apparatus 12 can generate the designated tomographic image, and therefore, the image processing apparatus 10 may not generate the designated tomographic image. In a case where the image interpretation apparatus 12 of the embodiment stores the plurality of projection images 45 in advance although the processing amount is increased with the generation of the designated tomographic image, the transmission/reception of any information with respect to the image processing apparatus 10 is not required after the image interpretation apparatus 12 has received the composite two-dimensional image, the depth map 43, and the plurality of projection images 45 from the image processing apparatus 10. Therefore, a load on communication can be reduced. In particular, in the image processing system 3 of the embodiment, high effects are obtained in a case where the interpreter repeats the generation of the designated tomographic image many times.

As described above, the image processing system 3 of the above-described embodiments comprises the acquisition unit 50, the tomographic image generation unit 52, the designated tomographic image generation unit 53, the composite two-dimensional image generation unit 54, the information generation unit 56, the display controller 72, and the acceptance unit 74. The acquisition unit 50 acquires a plurality of projection images obtained by tomosynthesis imaging in which radiation is emitted from the radiation source to the breast at different irradiation angles and a projection image is captured at each irradiation angle by the radiation detector. The tomographic image generation unit 52 generates a plurality of tomographic images in each of a plurality of tomographic planes of the breast, from the plurality of projection images. The composite two-dimensional image generation unit 54 generates a composite two-dimensional image from a plurality of images selected from among the plurality of projection images and the plurality of tomographic images. The information generation unit 56 generates the depth map 43 representing a correspondence relationship between a position in the composite two-dimensional image and the depth of the tomographic plane corresponding to the position. The display controller 72 performs control of causing the display unit 44 to display the composite two-dimensional image. The acceptance unit 74 accepts the region information representing the designated region designated with respect to the composite two-dimensional image displayed on the display unit 44. In a case where the acceptance unit 74 has accepted the region information, the designated tomographic image generation unit 53 generates a tomographic image in a tomographic plane at a specified depth on the basis of the depth map 43, which corresponds to the designated region in the composite two-dimensional image, as the designated tomographic image. Further, in a case where the designated tomographic image is generated, the display controller 72 performs control of causing the display unit 44 to display the generated designated tomographic image.

With the above-described configuration, in the image processing system 3 of the above-described embodiments, in a case where the designated region is designated from the composite two-dimensional image, a designated tomographic image in a tomographic plane at a specified depth can be generated on the basis of the depth map 43 and displayed. Thus, after the composite two-dimensional image and the depth map 43 are generated, the plurality of tomographic images 33 generated by the tomographic image generation unit 52 may not be stored.

Thus, with the above-described configuration, in the image processing system 3 of the above-described embodiments, it is possible to reduce a load associated with the handling of tomographic images.

Figure 14:
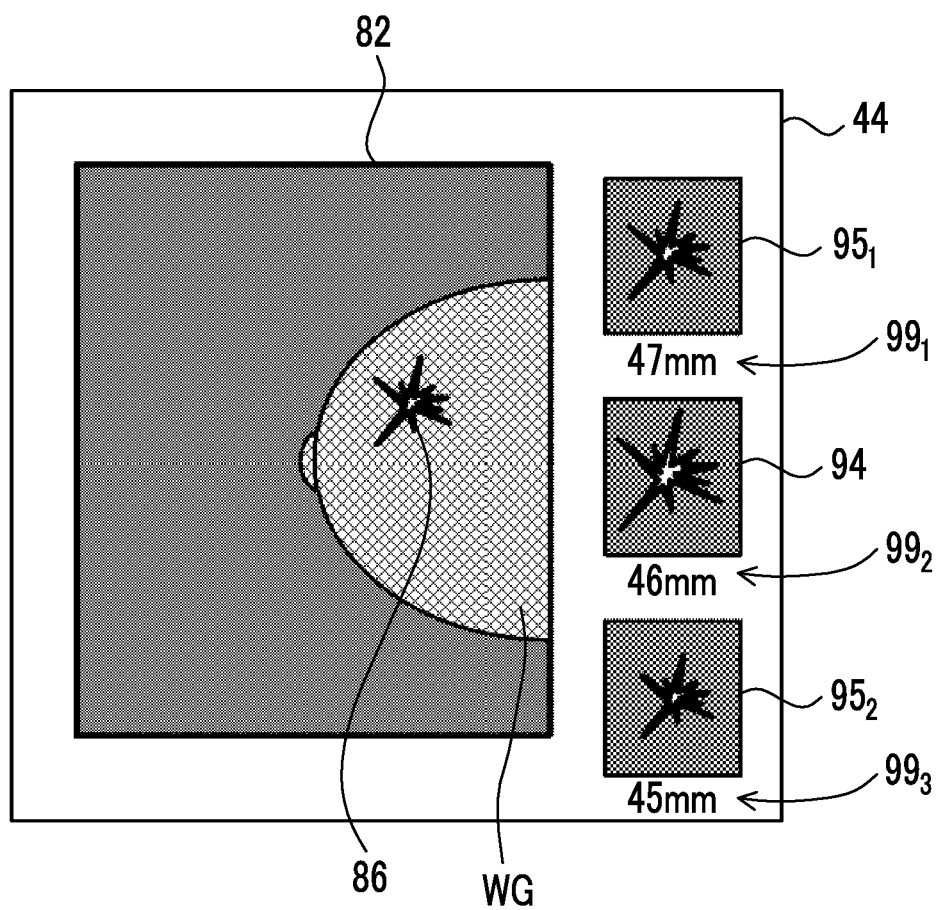
FIG. 14 is a diagram illustrating an example of a display form of a composite two-dimensional image, a designated tomographic image, tomographic images before and after the designated tomographic image.

In the above-described embodiments, an aspect in which the designated tomographic image generation unit 53 generates one designated tomographic image corresponding to a tomographic plane at a depth according to the depth information has been described, but the designated tomographic image generated by the designated tomographic image generation unit 53 is not limited to this aspect. For example, an aspect in which tomographic images corresponding to tomographic planes at depths before and after a depth according to the depth information are also generated by the designated tomographic image generation unit 53 and are displayed on the display unit 44 may be used. FIG. 14 illustrates an example of a display form in which a designated tomographic image 94 at a depth according to the depth information, tomographic images 951 and 952 corresponding to tomographic planes at depths before and after the depth according to the depth information are displayed on the display unit 44. In this case, since a plurality of tomographic images are displayed, it is preferable to display numerical values 991 to 993 respectively representing the depths of the tomographic planes of the designated tomographic image 94 and the tomographic images 951 and 952.

In the above-described embodiments, regarding the designated region, an aspect in which the acceptance unit 74 specifies the depth from the depth map 43 has been described, but an aspect in which the designated tomographic image generation unit 53 specifies the depth from the depth map 43 may be used.

Further, an aspect in which the image processing system 3 of the above-described embodiments comprises the tomographic image generation unit 52 and the designated tomographic image generation unit 53 as generation units has been described, but the present disclosure is not limited to the aspect. An aspect in which the image processing system 3 includes one generation unit having the functions of the tomographic image generation unit 52 and the designated tomographic image generation unit 53 may be used.

In addition, in the above-described embodiments, an aspect in which the image processing system 3 comprises the image preservation system 8, the image processing apparatus 10, and the image interpretation apparatus 12 has been described, but the present disclosure is not limited to the aspect, and for example, an aspect in which the image preservation system 8 and the image processing apparatus 10 are integrated may be used.

In the above-described embodiments, for example, the following various processors can be used as the hardware structure of processing units executing various kinds of processing, such as the tomographic image generation unit 52, the designated tomographic image generation unit 53, the composite two-dimensional image generation unit 54, the information generation unit 56, the storage controller 58, the transmission unit 60, the reception unit 62, the reception unit 70, the display controller 72, the acceptance unit 74, and the transmission unit 76. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (program) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

In addition, specifically, an electric circuit (circuitry) obtained by combining circuit elements, such as semiconductor elements, can be used as the hardware structure of the various processors.

In the above-described embodiments, an aspect in which the image generation processing program 31 is stored (installed) in the ROM 30B in advance and the image interpretation processing program 41 is stored (installed) in the ROM 40B in advance has been described, but the present disclosure is not limited thereto. Each of the image generation processing program 31 and the image interpretation processing program 41 may be provided by being recorded in a recording medium such as a compact disk read only memory (CD-ROM), a digital versatile disk read only memory (DVD-ROM), and a Universal Serial Bus (USB) memory. In addition, each of the image generation processing program 31 and the image interpretation processing program 41 may be downloaded from an external device via a network.

For example, the configurations and operations of the medical system 1, the radiography system 2, and the image processing system 3 described in the above-described embodiments are illustrative and may be modified in accordance with situations in a range without departing from the scope of the invention.

It goes without saying that the above-described embodiments can be combined appropriately.

What is claimed is:

1. An image processing system comprising:
   an acquisition unit that acquires a plurality of projection images obtained by tomosynthesis imaging in which radiation is emitted from a radiation source to a breast at different irradiation angles and a projection image is captured at each irradiation angle by a radiation detector;
   a reception unit that receives a composite two-dimensional image and correspondence relationship information representing a correspondence relationship between a position in the composite two-dimensional image and a depth of a tomographic plane corresponding to the position;
   a display controller that performs control of causing a display device to display the composite two-dimensional image;
   an acceptance unit that accepts region information representing a designated region designated with respect to the composite two-dimensional image displayed on the display device; and
   a designated tomographic image generation unit that generates, as a designated tomographic image, a tomographic image in a tomographic plane at a depth which corresponds to the designated region in the composite two-dimensional image and is specified on the basis of the correspondence relationship information, in a case where the acceptance unit accepts the region information, wherein
   the display controller further performs control of causing the display device to display the generated designated tomographic image.

2. The image processing system according to claim 1, wherein
   the designated tomographic image is a tomographic image of a portion corresponding to the designated region, in the tomographic plane at the depth specified according to a position of the designated region.

3. The image processing system according to claim 1, wherein
   the designated tomographic image is a tomographic image including an image of the entire breast, in the tomographic plane at the depth specified according to a position of the designated region.

4. The image processing system according to claim 1, wherein
   the designated tomographic image is a tomographic image of a portion corresponding to a region in a predetermined range including the designated region, in the tomographic plane at the depth specified according to a position of the designated region.

5. The image processing system according to claim 1, wherein
   the designated tomographic image generation unit further generates tomographic images in tomographic planes at predetermined depths before and after the depth of the designated tomographic image, and
   the display controller further performs control of causing the display device to display the generated tomographic images in the tomographic planes at the depths before and after the depth of the designated tomographic image.

6. The image processing system according to claim 1, wherein
   the display controller performs control of causing the display device to display the composite two-dimensional image and the designated tomographic image side by side.

7. The image processing system according to claim 1, wherein
   the display controller performs control of causing the display device to display the composite two-dimensional image and the designated tomographic image in a state in which the composite two-dimensional image and the designated tomographic image are at least partially superimposed on each other.

8. The image processing system according to claim 1, further comprising:

a storage controller that performs control of deleting the plurality of tomographic images from a storage unit, in a case where the plurality of tomographic images are stored in the storage unit after the composite two-dimensional image and the correspondence relationship information are received.

9. The image processing system according to claim 1, further comprising:

an image processing apparatus that includes a transmission unit that transmits the composite two-dimensional image, the correspondence relationship information, and the designated tomographic image to the display device, the acquisition unit, and the designated tomographic image generation unit; and the display device that includes a reception unit that receives the composite two-dimensional image, the correspondence relationship information, and the designated tomographic image from the image processing apparatus, the display controller, and the acceptance unit.

10. The image processing system according to claim 1, further comprising:

an image processing apparatus that includes a transmission unit that transmits the plurality of projection images, the composite two-dimensional image, and the correspondence relationship information, to the display device, the acquisition unit; and the display device that includes a reception unit that receives the plurality of projection images, the composite two-dimensional image, and the correspondence relationship information from the image processing apparatus, the designated tomographic image generation unit, the display controller, and the acceptance unit.

11. An image processing method executed by a computer, the method comprising:

accepting region information representing a designated region designated with respect to a composite two-dimensional image generated from a plurality of projection images obtained by tomosynthesis imaging;

from (a) a correspondence relationship between a position in the composite two- dimensional image and a depth of a tomographic plane corresponding to the position, (b) the plurality of projection images, and (c) the region information, generating, as a designated tomographic image, a tomographic image in a tomographic plane at a depth which corresponds to the designated region in the composite two-dimensional image and is specified on the basis of the correspondence; and outputting the generated designated tomographic image.

12. A non-transitory computer-readable storage medium storing an image processing program causing a computer to execute a process comprising:

acquiring a plurality of projection images obtained by tomosynthesis imaging in which radiation is emitted from a radiation source to a breast at different irradiation angles and a projection image is captured at each irradiation angle by a radiation detector;

receiving a composite two-dimensional image and correspondence relationship information representing a correspondence relationship between a position in the composite two-dimensional image and a depth of a tomographic plane corresponding to the position;

performing control of causing a display device to display the composite two-dimensional image;

accepting region information representing a designated region designated with respect to the composite two-dimensional image displayed on the display device;

generating, as a designated tomographic image, a tomographic image in a tomographic plane at a depth which corresponds to the designated region in the composite two-dimensional image and is specified on the basis of the correspondence relationship information, in a case where the region information is accepted; and further performing control of causing the display device to display the generated designated tomographic image.

* * * * *